United States Patent [19]

Sandlin et al.

[11] Patent Number: 5,098,428
[45] Date of Patent: Mar. 24, 1992

[54] CRYOSURGICAL SPRAYING APPARATUS

[76] Inventors: Felix M. Sandlin, 420 Tower Dr., San Antonio, Tex. 78232; Jack D. Waller, 2406 S. Lipscomb, Amarillo, Tex. 79109

[21] Appl. No.: 669,365
[22] Filed: Mar. 14, 1991
[51] Int. Cl.⁵ .............................................. A61B 17/36
[52] U.S. Cl. ....................................... 606/22; 606/20; 62/52.1; 62/293; 222/209
[58] Field of Search ................................... 606/20-26; 62/293, 51.1-52.1; 222/207-211, 468, 470, 631-633, 478

[56] References Cited

U.S. PATENT DOCUMENTS

| | | | |
|---|---|---|---|
| 3,534,739 | 10/1970 | Bryne | 606/22 |
| 3,651,813 | 3/1972 | Bryne | 128/200.14 |
| 3,739,956 | 6/1973 | Reynolds | 222/396 |
| 3,889,681 | 6/1975 | Waller et al. | 128/303.1 |
| 4,043,341 | 8/1977 | Tromovitch | 606/22 |
| 4,376,376 | 3/1983 | Gregory | 62/51.1 |
| 4,383,622 | 5/1983 | Guth | 222/209 |

Primary Examiner—Stephen C. Pellegrino
Assistant Examiner—Steven J. Shumaker
Attorney, Agent, or Firm—Donald R. Comuzzi

[57] ABSTRACT

An insulated, compact, mobile crysosurgical instrument is provided that has no moving parts in contact with a liquefied gas coolant retained in an insulated container. Upon interrupting normal venting from the container, the liquefied gas coolant will build up a pressure in the container which may be increased by a squeeze pressure device. That pressure will cause the liquefied gas coolant to spray from a nozzle until normal venting is restored.

6 Claims, 2 Drawing Sheets

CRYOSURGICAL SPRAYING APPARATUS

BACKGROUND OF THE INVENTION

The present invention relates to a cryosurgical instrument and, more particularly to a liquid nitrogen spray apparatus that can be used in treating lesions, benign or malignant, that respond to cryosurgery.

In the medical practice there have been various types of spraying apparatus used in cryosurgery for the treatment of skin lesions. Using layman's terms, the skin lesions may be any type of definite growth in the skin (warts being an example) or an infection in the skin (acne be an example). In recent years, cryosurgery has been used to treat cancerous or malignant tumors in the skin. The cancerous areas may be located on either the internal areas of the body or on the exterior skin.

Regardless of the type of cryosurgical instrument that is used, the lesion must be frozen to at least $-20°$ C. to insure the destruction of all the abnormal cells. Though, various types of liquefied gas coolants may be used in cryosurgical instruments, the usual liquefied gas used by the medical profession is liquid nitrogen which has a boiling point of $-196°$ C. Because of the extremely low temperature of the liquid nitrogen, it must be stored in special containers to prevent evaporation into the atmosphere. Also, if any moving parts come into contact with the liquid nitrogen, they may freeze up or stick due to a moisture collection from the atmosphere. Any flexible hosing that may come in contact with the liquid nitrogen becomes very rigid and brittle. Many early cryosurgical instruments, such as the one shown in U.S. Pat. No. 3,739,956, issued to Reynolds, used various types of valving apparatus and moving parts which came into contact with the liquid refrigerant. Due to the extreme cold, all the valving apparatus would freeze up in a very short period of time causing the liquid coolant to rapidly evaporate into the atmosphere. Those cryosurgical instruments were not only wasteful of the liquefied gas but were also fairly complex and expensive to manufacture.

Another common apparatus, such as the ones shown in U.S. Pat. Nos. 3,534,739 and 3,651,813, contained no moving parts in contact with the liquefied gas coolant. However, those instruments were closed systems which caused the coolant to continuously boil inside the container and completely evaporate in a very short period of time. When normal venting is stopped, pressure built up in the container causes a stream of coolant to be ejected from the nozzle. In a single operation of thirty minutes or more, the container would have to be filled repeatedly because many operations require numerous treatments of the lesions by the liquid gas coolant to insure its complete destruction. Although the above apparatus' are inexpensive to manufacture, they are extremely wasteful of liquid coolant as well as being impossible to use for repeated time interval treatments without coolant refills.

A third type of cryosurgical instrument, such as the TT-32 Liquid Nitrogen Sprayer, by Physicians Products, Inc., Box 44, Millbrae, Calif. 94030, used vacuum bottles to avoid coolant waste and further contained a valving mechanism to allow normal venting of pressure built in the vacuum bottle. That normal venting would dissipate the pressure sufficiently so that there would be no continuous ejection of liquid coolant from the nozzle. To facilitate operation, these instruments were provided with a squeeze bulb to increase the pressure in the vacuum bottle once the valving mechanism was closed. Unfortunately, these systems were designed with the valve mechanism being of a screw type and being situated immediately above the squeeze bulb. That configuration made the instrument inconvenient to operate and in many instances required two people to insure proper use. Furthermore, after squeezing the squeeze bulb with the valve closed, liquid nitrogen is ejected from the nozzle and will continue to eject until the pressure inside the vacuum bottle has been dissipated. That may result in an excess of the liquid coolant reaching the skin lesion or adjacent normal areas with resultant damage to skin tissue. Because the valve is a screw type valve, it is not easy to rapidly open and close resulting in a loss of the delicate control of the amount of coolant delivered which is so highly desirable in such a unit especially in treating very sensitive areas about the eyes, face, genitalia, etc. Although these instruments are inexpensive and do not waste liquid nitrogen as long as the vent valve remains open, there use under hospital conditions is very awkward and inconvenient.

To overcome the above problems, a cryosurgical spraying apparatus, disclosed in U.S. Pat. No. 3,889,681, issued to the inventor of the present application and herein incorporated by reference, was produced with a continuous open vent provided immediately above the squeeze bulb which may be closed by placing the thumb over the opening. When the thumb is removed from the opening, the pressure inside the vacuum bottle immediately decreases to stop the ejection of the liquid coolant. That venting mechanism provides an extremely delicate and precise control of the amount of coolant delivered. Although that system is far superior to any of the preceding systems, it too is in many instances awkward and inconvenient to use as well as more expensive to manufacture than the present invention.

The position of the open vent directly above the squeeze bulb makes it difficult to pump the bulb to initiate a steady stream of liquid coolant while still maintaining the vent closed with the thumb of that hand.

Therefore, the design, as embodied in the present invention, has been improved by moving the vent to a position on the cap directly below the nozzle. That position allows a user to securely hold the instrument with one hand and use a index finger of that hand to cover and uncover the vent. Thus, the opposite hand is freed to squeeze the bulb as needed or provide some other necessary medical movement or operation. It further prevents an excess of liquid coolant from being applied to the skin lesion because of the extremely precise and delicate control made possible by the finger control venting. The present invention also incorporates a standard Leur lock-head for the rapid and easy attachment of tips (needles) of any diameter and length necessary to treat lesions of any size and location.

SUMMARY OF THE INVENTION

It is an object of the present invention to provide a cryosurgical instrument for treating skin lesions, benign or malignant.

It is another object of the present invention to provide an insulated, compact, mobile cryosurgical instrument that is very easy to use and inexpensive to manufacture.

It is a further object of the present invention to provide a cryosurgical instrument that minimizes waste of liquid coolant, such as nitrogen. It is yet a further object of the present invention to provide a cryosurgical instrument with no moving parts that contact the liquid coolant and, simultaneously, be very economical to manufacture and easy to use in a hospital or office.

It is yet another object of the present invention to provide an insulated, compact, mobile cryosurgical instrument wherein pressure can be applied to the liquefied gas coolant and released immediately by movement of one finger while still easily maintaining the nozzle on the skin lesion being treated.

DESCRIPTION OF THE PREFERRED EMBODIMENT

Figure 1:
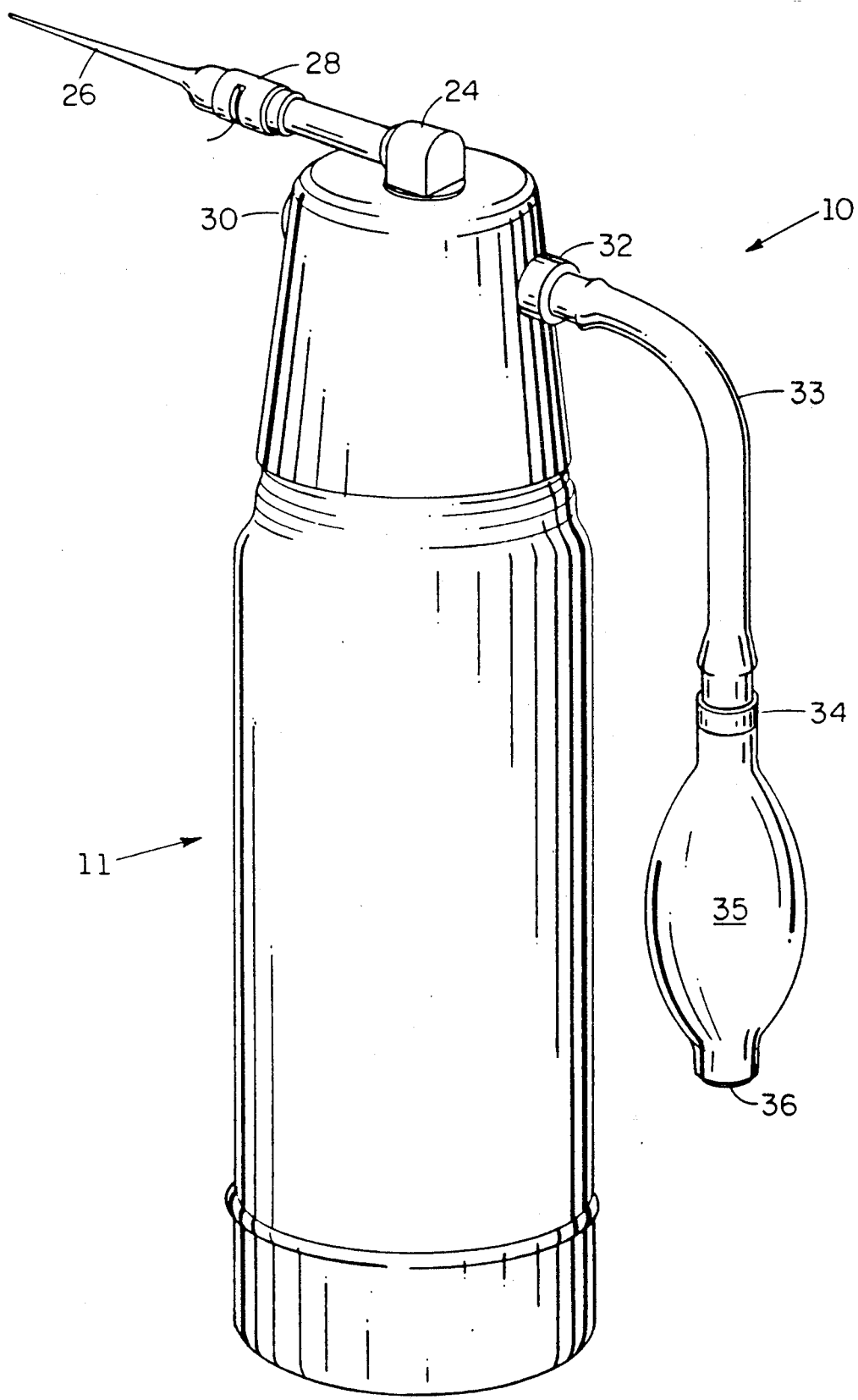
FIG. 1 is a perspective view of the cryosurgical spraying apparatus.
Figure 2:
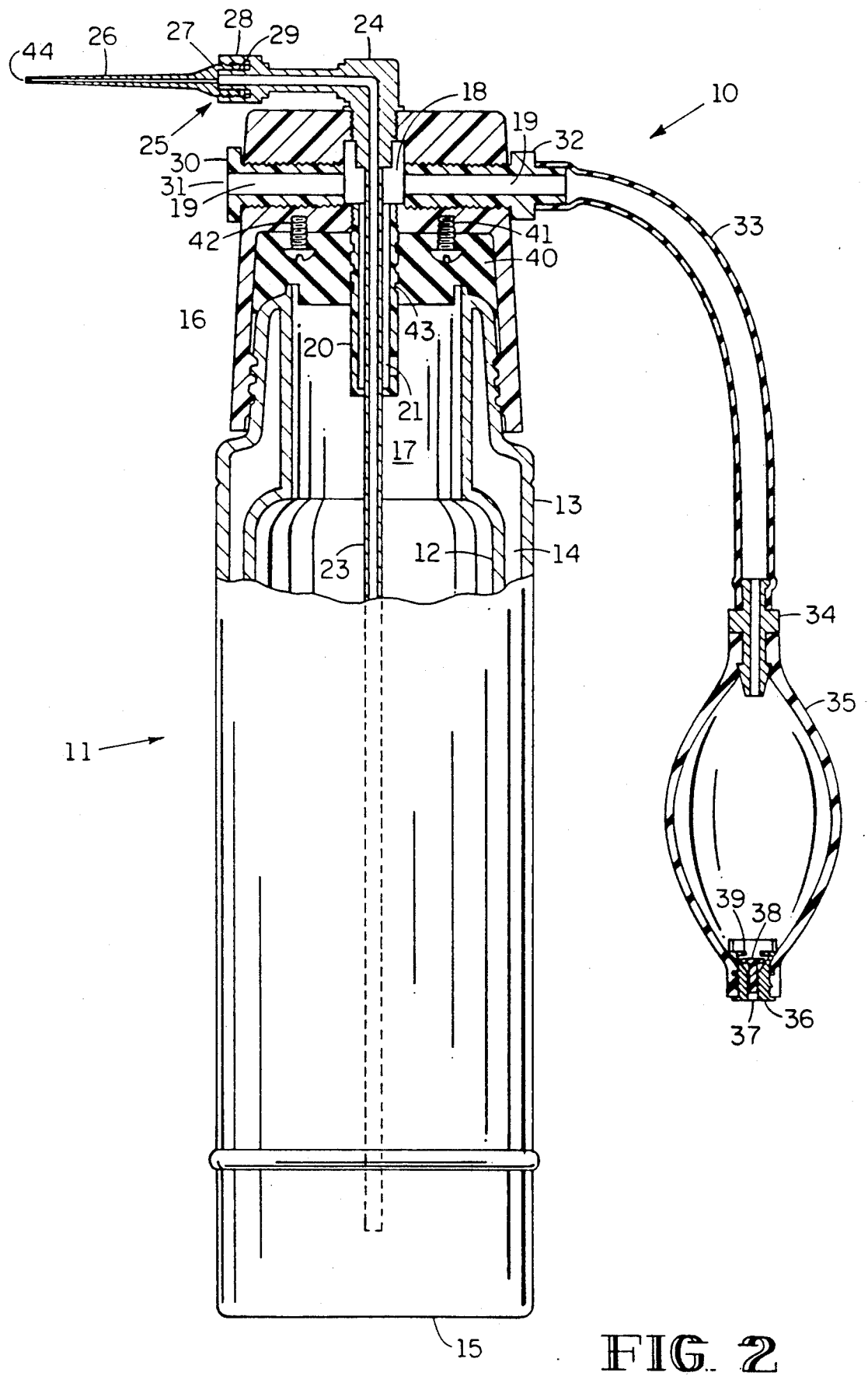
FIG. 2 is an elevated cross-sectional view of the cryosurgical spraying apparatus.

Referring now to FIGS. 1 and 2 in combination, the cryosurgical spraying apparatus is represented generally by reference numeral 10. Cryosurgical spraying apparatus 10 has an insulated container 11 that is similar to a common vacuum bottle. Insulated container 11 has an inner wall 12 and outer wall 13 with a space 14 contained therebetween. Space 14 also extends between the bottom of inner wall 12 (not shown) and bottom 15 of outer wall 13. The upper portion of insulated container 10 consists of cap 16 threadably connected to the upper portion of outer wall 13. The upper portion of insulated container 11 contains opening 17 through which a liquefied gas coolant may be inserted upon removing cap 16.

Cap 16 has vertical passage 18 and horizontal passage 19 contained therein. Passages 18 and 19 cross to form a T in cap 16. Cylinder 20, made of plastic in the preferred embodiment, is threadably connected to the lower portion of passage 18 and extends into opening 17. Cylinder 20 contains passage 21 which decreases the diameter of passage 18 as it opens into insulated container 11. Tubing 23 extends through passages 18 and 21 to nearly the bottom of inner wall 12. Tubing 23 should be of a suitable, non-corrosive metal substance for receiving a liquefied gas coolant contained inside of insulated container 11. The upper portion of tubing 23 which extends through passage 18 has a 90° bend 24 to the left. Tubing 23 is threadably connected to the upper portion of passage 18 immediately below 90° bin 24. In the preferred embodiment, an epoxy type sealant is used to secure tubing 23 to cap 16.

The left most portion of 90 degree bend 24 provides a large nozzle 25 to which needle 26 may be attached. Large nozzle 25 has Leur type locking head formed by inner tubing 27 and outer structure 28 for retaining needle 26. Slots 29 have been provided in outer structure 28 to provide ease of installation of needle 26 by preventing the trapping of pressurized air behind needle 26. Needle 26 has a small tip to provide the application of liquefied gas coolant to a very localized area. Other types of needles or nozzles may be used according to the particular needs of the individual case.

Finger press flange 30 containing opening 31 is threadably connected to passage 19 where it opens from cap 16 below large nozzle 25. Excess pressure is vented from insulated container 11 through a small hole (not shown) in cylinder 20 into passage 21 and subsequently out passage 19 through opening 31 of finger press flange 30. That venting makes the present invention an open system which prevents the wasteful ejection of liquid coolant through nozzle 25 due to excessive pressures in insulated container 11. In the preferred embodiment, finger press flange 30 is sealed in passage 19 by a clear epoxy type sealant.

Flange fitting 32 is threadably connected to the opposite end of passage 19 from finger press flange 30. In the preferred embodiment, flange fitting 32 is sealed in passage 19 by a clear epoxy type sealant. Flexible rubber hose 33 is connected to flange fitting 32 for fluid communication with the inside of insulated container 11. The opposite end of flexible rubber hose 33 is connected to one end of double-sided flange fitting 34. The opposite end of flange fitting 34 is connected to squeeze bulb 35 which may be utilized to pressure the inside of insulated container 11 via flange fittings 34 and 32, tubing 33, passages 19 and 21, and the small hole (not shown) in cylinder 20 opening into space 17 when opening 31 of flange 30 is covered. The bottom of squeeze bulb 35 has a one way valve 36 that allows air to flow into squeeze bulb but not vice-versa. Valve 36 consists of an opening 37 inside valve 68 which is covered with T-stop 38. Upon squeezing squeeze bulb 35, T-stop 38 is pressed against tab 39 to cover opening 37 and prevent the escape of air through that opening.

The section of cap 16 denoted by numeral 40 is filled with sealant to firmly hold cylinder 20 in place and seal any leaks. In the preferred embodiment, epoxy is used as the sealant. Screws 41, 42, and grooves 43 in cylinder 20 are to provide support for the sealant and prevent its moving about or dislodging from cap 16.

In the present invention, needle 26 is shown with a small tip 44; however, other types of needles or nozzles may be used including a nozzle that would spray a large area for treatment of skin conditions such as acne. Particular types of spraying attachments may be desirable when treating a cancerous growth, or other skin lesions. Many other types of needles may be utilized depending upon the particular situation.

METHOD OF OPERATION

Cap 16 is unscrewed from insulated container 11. A liquefied gas coolant is then poured through opening 17 into insulated container 11 and cap 16 is placed back on insulated container 11. Cap 24 should be sufficiently tighten to provide a good seal with outer wall 13. The liquefied gas coolant inside of insulated container 11 (usually liquid nitrogen) needs a vent to the atmosphere to keep excessive pressure from building up because of the extremely low temperature. In cryosurgical spraying apparatus 10, a vent is provided through the small hole (not shown) of cylinder 20, passage 21 of cylinder 20, passage 19 and out opening 31 of finger flange 30. Normally one filling of insulated container 11 will last an entire working day of eight hours without refilling.

Whenever cryosurgical spraying apparatus 10 is needed a person such as a medical doctor could immediately pick up the apparatus, put small tip 44 of needle 26 to the area being treated and squeeze bulb 35 while simultaneously placing one finger of the hand holding cryosurgical spraying apparatus 10 over opening 31 of flange 30. The squeezing of squeeze bulb 35 will create a pressure inside of insulated container 11 thereby forcing the liquefied gas coolant up tubing 23 through 90 bin 24 and out through needle 26. As soon as the desired amount of liquefied gas coolant has been applied to the skin lesion, the finger covering opening 31 may be removed from flange 30 thereby opening the system. That will immediately relieve the pressure inside of insulated container 11 thereby stopping the flow of liquefied gas coolant out needle 26. That process may be repeated as many times as cryosurgical treatment is necessary during an operation. Because the container is well insulated the liquefied gas coolant will last for an extended period of time for repeated treatments.

In the present apparatus there are no moving parts that will come in contact with the liquefied gas coolant and therefor be subject to freezing due to moisture condensation. Also pressure inside of the container can be relieved immediately by simply removing the index finger from flange 30, thereby stopping the flow of liquefied gas coolant thus enabling the treating physician to apply a very controlled amount of an localized area.

Although the present invention has been described in terms of the foregoing preferred embodiment, such description has been exemplary purposes only and, as will be apparent to those of ordinary skill in the art, many alternatives, equivalence and variations of varying degrees will fall within the scope of the present invention. That scope, accordingly, is not to be limited in any respect by the foregoing description but, rather, is designed only by the claims which file.

We claim:

1. A cryosurgical instrument for treating skin lesions comprising:
    an insulated container for holding a liquefied gas coolant;
    cap means for said insulated container, said cap means having a first passage extending vertically through said cap means and a second passage extending horizontally through said cap means;
    tubing means extending from near the bottom of said insulated container through said first passage and to the outside thereof;
    a pressure line connected to a first opening of said second passage and communicating with the inside of said insulated container;
    a vent means formed by a second opening of said second passage and communicating with the inside of said insulated container;
    nozzle means attached to said tubing means for spraying said liquefied gas coolant upon pressurization from said pressure line; and
    said pressure line being connected to a source of pressurized air, wherein said vent means must be covered before pressurization.

2. The cryosurgical instrument as recited in claim 1 wherein said source of pressurized air comprises a manual squeeze bulb.

3. The cryosurgical instrument as recited in claim 2 wherein said instrument is adapted to be held with one hand by an operator so that a finger of that hand may be used to cover said vent means before pressurization and to instantaneously remove pressurization upon uncovering said vent means.

4. The cryosurgical instrument as recited in claim 3 wherein said pressure line, said vent means, and said tubing means extend through said cap means in an air tight manner.

5. The cryosurgical instrument as recited in claim 4 wherein said insulated container is a vacuum bottle and said cap means is a cap for said vacuum bottle.

6. The cryosurgical instrument as recited in claim 1 wherein said nozzle means is interchangeable.

* * * * *